United States Patent
Niazi et al.

(10) Patent No.: US 12,098,177 B2
(45) Date of Patent: Sep. 24, 2024

(54) TARGETED IL-12 TREATMENTS AND METHODS TO STIMULATE haNK AND NK92mi CELLS

(71) Applicant: NantBio, Inc., Culver City, CA (US)

(72) Inventors: Kayvan Niazi, Culver City, CA (US); Clifford Anders Olson, Culver City, CA (US); Shiho Tanaka, Culver City, CA (US); Heather McFarlane, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 632 days.

(21) Appl. No.: 17/274,127

(22) PCT Filed: Sep. 5, 2019

(86) PCT No.: PCT/US2019/049797
§ 371 (c)(1),
(2) Date: Mar. 5, 2021

(87) PCT Pub. No.: WO2020/051363
PCT Pub. Date: Mar. 12, 2020

(65) Prior Publication Data
US 2022/0289805 A1    Sep. 15, 2022

Related U.S. Application Data

(60) Provisional application No. 62/728,510, filed on Sep. 7, 2018.

(51) Int. Cl.
*C07K 14/54* (2006.01)
*A61K 35/17* (2015.01)
*C12N 5/0783* (2010.01)

(52) U.S. Cl.
CPC .......... *C07K 14/5434* (2013.01); *A61K 35/17* (2013.01); *C12N 5/0646* (2013.01); *C07K 2317/24* (2013.01); *C07K 2317/55* (2013.01); *C07K 2317/622* (2013.01); *C07K 2319/01* (2013.01); *C07K 2319/33* (2013.01)

(58) Field of Classification Search
CPC .......... C07K 14/5434; C07K 2317/24; C07K 2317/55; C07K 2317/622; C07K 2319/01; C07K 2319/33; A61K 35/17; C12N 5/0646
See application file for complete search history.

(56) References Cited

U.S. PATENT DOCUMENTS

| | | | |
|---|---|---|---|
| 8,034,332 B2 | 10/2011 | Klingemann | |
| 8,945,571 B2 * | 2/2015 | Mossner | A61P 35/00 435/69.6 |
| 10,688,182 B2 * | 6/2020 | Chen | C07K 16/18 |
| 11,129,883 B2 * | 9/2021 | Marcus | A61K 47/6811 |
| 2017/0166620 A1 | 6/2017 | Strittmatter et al. | |
| 2018/0200366 A1 | 7/2018 | Wong et al. | |

FOREIGN PATENT DOCUMENTS

| | | | |
|---|---|---|---|
| CN | 108250303 A | 7/2018 | |
| WO | 2016160602 A2 | 10/2016 | |
| WO | WO-2018075989 A1 * | 4/2018 | ........... A61K 38/005 |
| WO | 2018183169 A1 | 10/2018 | |
| WO | 2020/051363 A1 | 3/2020 | |

OTHER PUBLICATIONS

Sela-Culang et al., The structural basis of antibody-antigen recognition, 2013, Frontiers in Immunology, vol. 4, Article 302, pp. 1-13 (Year: 2013).*
Kussie et al, A Single Engineered Amino Acid Substitution Changes Antibody Fine Specificity, 1994, Journal of Immunology, pp. 146-152 (Year: 1994).*
Cooper et al., The Development and Causes of Cancer, 2000, The Cell: A Molecular Approach, 2nd edition (Year: 2000).*
Tugues et al., New insights into IL-12-mediated tumor suppression, 2014, Cell Death & Differentiation, vol. 22, pp. 237-246 (Year: 2014).*
Lasek et al., Interleukin 12:still a promising candidate for tumor immunotherapy?, 2014, Cancer Immunology, Immunotherapy, vol. 63, pp. 419-435 (Year: 2014).*
Heppner and Miller, Tumor heterogeneity: biological implications and therapeutic consequences, 1983, Cancer Metastasis Reviews, vol. 2, pp. 5-23 (Year: 1983).*
"NK92MI (ATCC® CRL2408™)", ATCC, American Type Culture Collection, 3 pages.
Charych et al., "NKTR-214, an Engineered Cytokine with Biased IL2 Receptor Binding, Increased Tumor Exposure, and Marked Efficacy in Mouse Tumor Models", Clin Cancer Res, Feb. 1, 2016, vol. 22, No. 3, pp. 680-690.
Fallon et al., "The immunocytokine NHS-IL 12 as a potential cancer therapeutic", Oncotarget, Mar. 24, 2014 , vol. 5, No. 7, pp. 1869-1884.
Hodge et al., "Regulation of Nuclear Gamma Interferon Gene Expression by Interleukin 12 (IL-12) and IL-2 Represents a Novel Form of Posttranscriptional Control", Molecular and Cellular Biology, Mar. 2002, vol. 22, No. 6, pp. 1742-1753.

(Continued)

*Primary Examiner* — Jeffrey Stucker
*Assistant Examiner* — Brittney E Donoghue
(74) *Attorney, Agent, or Firm* — Martin Fessenmaier; Umberg Zipser LLP

(57) ABSTRACT

Compositions and methods for NK cell based treatments, and particularly NK cells that express and intracellularly retain IL-2, are presented in which the NK cells are stimulated with a chimeric protein that has a cancer cell targeting portion and an IL-12 portion. Beneficially, such chimeric protein has substantially reduced systemic toxicity and induces IFN-γ secretion in a targeted manner. Moreover, chimeric proteins contemplated herein also significantly enhanced IFN-γ secretion in NK cells that express and intracellularly retain IL-2 as compared to native NK cells. Preferred chimeric proteins comprise SEQ ID NO:1 or SEQ ID NO:2, and SEQ ID NO:3.

17 Claims, 4 Drawing Sheets
Specification includes a Sequence Listing.

(56) References Cited

OTHER PUBLICATIONS

International Search Report and Written Opinion received for PCT Application Serial No. PCT/US2019/049797 dated Dec. 27, 2019, 15 pages.

Jochems et al., "An NK cell line (haNK) expressing high levels of granzyme and engineered to express the high affinity CD16 allele", Oncotarget, 2016, vol. 7, No. 52, pp. 86359-86373.

Konstantinidis et al., "Targeting IL-2 to the endoplasmic reticulum confines autocrine growth stimulation to NK-92 cells", Experimental Hematology, 2005, vol. 33, pp. 159-164.

Nagashima et al., "Stable Transduction of the Interleukin-2 Gene Into Human Natural Killer Cell Lines and Their Phenotypic and Functional Characterization In Vitro and In Vivo", Blood, May 15, 1998, vol. 91, No. 10, pp. 3850-3861.

Ohshima et al., "Effect of IL 12 family cytokines on NK92 cells", J Osaka Dent Univ, Oct. 2017, vol. 51, No. 2, pp. 115-123.

Valedkarimi et al., "Antibody-cytokine fusion proteins for improving efficacy and safety of cancer therapy", Biomedicine & Pharmacotherapy, 2017, vol. 95, pp. 731-742.

Vignali et al., "IL-12 Family Cytokines: Immunological Playmakers", Nat Immunol., vol. 13, No. 8, pp. 722-728.

Wang et al., "Interleukin-2 enhances the response of natural killer cells to interleukin-12 through up-regulation of the interleukin-12 receptor and STAT4", Blood, May 15, 2000, vol. 95, No. 10, pp. 3183-3190.

Ye et al., "Cellular and molecular mechanisms of IFN-γ production induced by IL-2 and IL-12 in a human NK cell line", Journal of Leukocyte Biology, 1995, vol. 58, pp. 225-233 (Cited from Specification).

Bruhns et al., "Specificity and affinity of human Fcγ receptors and their polymorphic variants for human IgG subclasses", Blood, 2009, vol. 113, No. 16, 3716-3725 (Cited from Specification).

Tam et al., "Characterization of genetically altered, interleukin 2-independent natural killer cell lines suitable for adoptive cellular immunotherapy", Human Gene Therapy, 2004, vol. 10, No. 8, pp. 1359-1373 (Cited from Specification).

Soman et al., "MTS dye based colorimetric CTLL-2 cell proliferation assay for product release and stability monitoring of interleukin-15: assay qualification, standardization and statistical analysis", Journal of Immunological Methods, 2009, vol. 348, No. 1-2, 31, pp. 83-94 (Cited from Specification).

Charych et al., "Modeling the receptor pharmacology, pharmacokinetics, and pharmacodynamics of NKTR-214, a kinetically-controlled interleukin-2 (IL2) receptor agonist for cancer immunotherapy", Plos One, 2017, vol. 12, No. 7, e0179431, pp. 1-24 (Cited from Specification).

International Preliminary Report on Patentability chapter I received for International PCT Application Serial No. PCT/US2019/049797 dated Mar. 18, 2021, 11 pages.

\* cited by examiner

Leader Peptide / Mouse scIL-12 / hu51-4 Heavy Chain

MCHQQLVISWFSLVFLASPL MWELEKDVYVVEVDWTPDAPGETVNLTCDTPEEDDITWTSDQRHGVISGKTLTITVKEFLDAGQYTCHKGGETLSHSHLLLHKKENGIWSTEILKNFKNKTFLKCEA
PNYSGRFTCSWLVQRNMDLKFNIKSSSSSPDSRAVTCGMASLSAEKVTLDQRDEKYSVSCQEDVTCPAEETLPIELALEARQQNKYENYSTSFFIRDIIKPDPPKNLQMKPLANSQVEVSWEYPDS
WSTPHSYFSLKFFVRIQRKKEMKETEGCNQKGAFLVEKTSTEVQCKGGNVCVQAQDRYNSCSSWACVPCRVRSGGGGSGGGGSGGGGSRVIPVSGPARCLSQSRNLLKTTDDMVKTAREKL
KHYSCTAEDIDHKDITRDQTSIKNCPLELHKNESCLATRETSSTTRGSCLPPQKSLMMTLCLGSIYEDLKMYQTEFQAINAALQNHNHQQIILDKMLVAIDELMQSLNHNGETILRQPKPVGEAD
PYRVKMKLCILHAFSTRVVTINRVMGYLSSA LEQVLVQSGGGLVKPGGSLRLSCAASGYTFTRYWMHWVRQAPGQGLEWIGAIYPGNSDTSYNQKFKGKATITADTSTNTAYMELSSLRSEDTAV
YYCARGEHLGSRRWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

Leader Peptide / Human scIL-12 / hu51-4 Heavy Chain

MCHQQLVISWFSLVFLASPL WELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLR
CEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLPLKNSRQVEVSWEYPD
TWSTPHSYFSLMFCVQVGSKREKDVFTDKTSATVICRKNASISVRAQDRYYSSSWSEWASVPCSSGGGSGGGGSGGGGSIWELHMYQQVEFKTMNAKLIMDPKRQIFLDQNMLAVIDELMQAINENSETVPQASSLEEPDFYKTKIKL
CILLHAERIRAVTIDRVMSYLNAS LEQVLVQSGGGLVKPGGSLRLSCAASGYTFTERYWMHWVRQAPGQGLEWIGAIYPGNSDTSYNQKFKGKATITADTSTNTAYMELSSLRSEDTAVYYCARGEEI
GSRRWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLSPGK

Leader Peptide / Hu51-4 Light Chain IVLTQSPATLSLSPGERATLSCRARQSISNYLHWYQQKPGQAPRLLIYYASQSISGIPDRFSGSGSGTDFTLTISRLEPEDFAVYCQQSNSWPLTFGQGTKVEIKRTV MDFQVQIFSFLLISASVAMSRGE
AAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Fig. 4

SEQUENCE LISTING

```
<160> NUMBER OF SEQ ID NOS: 3

<210> SEQ ID NO 1
<211> LENGTH: 994
<212> TYPE: PRT
<213> ORGANISM: Artificial Sequence
<220> FEATURE:
<223> OTHER INFORMATION: Chimeric Sequence for leader peptide/mouse
      scIL-12/hu51-4 heavy chain

<400> SEQUENCE: 1
```

```
Met Cys His Gln Gln Leu Val Ile Ser Trp Phe Ser Leu Val Phe Leu
1               5                   10                  15

Ala Ser Pro Leu Met Trp Glu Leu Glu Lys Asp Val Tyr Val Val Glu
            20                  25                  30

Val Asp Trp Thr Pro Asp Ala Pro Gly Glu Thr Val Asn Leu Thr Cys
            35                  40                  45

Asp Thr Pro Glu Glu Asp Ile Thr Trp Thr Ser Asp Gln Arg His
        50                  55                  60

Gly Val Ile Gly Ser Gly Lys Thr Leu Thr Ile Thr Val Lys Glu Phe
65                  70                  75                  80

Leu Asp Ala Gly Gln Tyr Thr Cys His Lys Gly Gly Glu Thr Leu Ser
                85                  90                  95

His Ser His Leu Leu His Lys Lys Glu Asn Gly Ile Trp Ser Thr
            100                 105                 110

Glu Ile Leu Lys Asn Phe Lys Asn Lys Thr Phe Leu Lys Cys Glu Ala
            115                 120                 125

Pro Asn Tyr Ser Gly Arg Phe Thr Cys Ser Trp Leu Val Gln Arg Asn
    130                 135                 140

Met Asp Leu Lys Phe Asn Ile Lys Ser Ser Ser Ser Pro Asp Ser
145                 150                 155                 160

Arg Ala Val Thr Cys Gly Met Ala Ser Leu Ser Ala Glu Lys Val Thr
                165                 170                 175

Leu Asp Gln Arg Asp Tyr Glu Lys Tyr Ser Val Ser Cys Gln Glu Asp
            180                 185                 190

Val Thr Cys Pro Thr Ala Glu Thr Leu Pro Ile Glu Leu Ala Leu
            195                 200                 205

Glu Ala Arg Gln Gln Asn Lys Tyr Glu Asn Tyr Ser Thr Ser Phe Phe
210                 215                 220

Ile Arg Asp Ile Ile Lys Pro Asp Pro Pro Lys Asn Leu Gln Met Lys
225                 230                 235                 240

Pro Leu Lys Asn Ser Gln Val Glu Val Ser Trp Glu Tyr Pro Asp Ser
            245                 250                 255

Trp Ser Thr Pro His Ser Tyr Phe Ser Leu Lys Phe Phe Val Arg Ile
            260                 265                 270

Gln Arg Lys Lys Glu Lys Met Lys Glu Thr Glu Glu Gly Cys Asn Gln
            275                 280                 285

Lys Gly Ala Phe Leu Val Glu Lys Thr Ser Thr Glu Val Gln Cys Lys
    290                 295                 300

Gly Gly Asn Val Cys Val Gln Ala Gln Asp Arg Tyr Tyr Asn Ser Ser
305                 310                 315                 320

Cys Ser Lys Trp Ala Cys Val Pro Cys Arg Val Arg Ser Gly Gly Gly
            325                 330                 335

Gly Ser Gly Gly Gly Gly Ser Gly Gly Gly Gly Ser Arg Val Ile Pro
            340                 345                 350

Val Ser Gly Pro Ala Arg Cys Leu Ser Gln Ser Arg Asn Leu Leu Lys
            355                 360                 365

Thr Thr Asp Asp Met Val Lys Thr Ala Arg Glu Lys Leu Lys His Tyr
    370                 375                 380

Ser Cys Thr Ala Glu Asp Ile Asp His Lys Asp Ile Thr Arg Asp Gln
385                 390                 395                 400

Thr Ser Thr Leu Lys Thr Cys Leu Pro Leu Glu Leu His Lys Asn Glu
            405                 410                 415
```

-continued

```
Ser Cys Leu Ala Thr Arg Glu Thr Ser Ser Thr Arg Gly Ser Cys
            420                 425                 430

Leu Pro Pro Gln Lys Thr Ser Leu Met Met Thr Leu Cys Leu Gly Ser
        435                 440                 445

Ile Tyr Glu Asp Leu Lys Met Tyr Gln Thr Glu Phe Gln Ala Ile Asn
    450                 455                 460

Ala Ala Leu Gln Asn His Asn His Gln Gln Ile Ile Leu Asp Lys Gly
465                 470                 475                 480

Met Leu Val Ala Ile Asp Glu Leu Met Gln Ser Leu Asn His Asn Gly
                485                 490                 495

Glu Thr Leu Arg Gln Lys Pro Val Gly Glu Ala Asp Pro Tyr Arg
        500                 505                 510

Val Lys Met Lys Leu Cys Ile Leu Leu His Ala Phe Ser Thr Arg Val
        515                 520                 525

Val Thr Ile Asn Arg Val Met Gly Tyr Leu Ser Ser Ala Leu Glu Gln
        530                 535                 540

Val Gln Leu Val Gln Ser Gly Ala Glu Val Lys Lys Pro Gly Ala Ser
545                 550                 555                 560

Val Lys Val Ser Cys Lys Ala Ser Gly Tyr Thr Phe Thr Arg Tyr Trp
                565                 570                 575

Met His Trp Val Arg Gln Ala Pro Gly Gln Gly Leu Glu Trp Ile Gly
            580                 585                 590

Ala Ile Tyr Pro Gly Asn Ser Asp Thr Ser Tyr Asn Gln Lys Phe Lys
            595                 600                 605

Gly Lys Ala Thr Ile Thr Ala Asp Thr Ser Thr Asn Thr Ala Tyr Met
        610                 615                 620

Glu Leu Ser Ser Leu Arg Ser Glu Asp Thr Ala Val Tyr Tyr Cys Ala
625                 630                 635                 640

Arg Gly Glu Glu Ile Gly Ser Arg Arg Trp Phe Ala Tyr Trp Gly Gln
                645                 650                 655

Gly Thr Leu Val Thr Val Ser Ser Ala Ser Thr Lys Gly Pro Ser Val
            660                 665                 670

Phe Pro Leu Ala Pro Ser Ser Lys Ser Thr Ser Gly Gly Thr Ala Ala
            675                 680                 685

Leu Gly Cys Leu Val Lys Asp Tyr Phe Pro Glu Pro Val Thr Val Ser
    690                 695                 700

Trp Asn Ser Gly Ala Leu Thr Ser Gly Val His Thr Phe Pro Ala Val
705                 710                 715                 720

Leu Gln Ser Ser Gly Leu Tyr Ser Leu Ser Ser Val Val Thr Val Pro
                725                 730                 735

Ser Ser Ser Leu Gly Thr Gln Thr Tyr Ile Cys Asn Val Asn His Lys
            740                 745                 750

Pro Ser Asn Thr Lys Val Asp Lys Lys Val Glu Pro Lys Ser Cys Asp
        755                 760                 765

Lys Thr His Thr Cys Pro Pro Cys Pro Ala Pro Glu Leu Leu Gly Gly
    770                 775                 780

Pro Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Arg Glu Glu Gln Tyr Asn Ser Thr Tyr Arg
```

```
                835                 840                 845
Val Val Ser Val Leu Thr Val Leu His Gln Asp Trp Leu Asn Gly Lys
    850                 855                 860
Glu Tyr Lys Cys Lys Val Ser Asn Lys Ala Leu Pro Ala Pro Ile Glu
865                 870                 875                 880
Lys Thr Ile Ser Lys Ala Lys Gly Gln Pro Arg Glu Pro Gln Val Tyr
                885                 890                 895
Thr Leu Pro Pro Ser Arg Asp Glu Leu Thr Lys Asn Gln Val Ser Leu
            900                 905                 910
Thr Cys Leu Val Lys Gly Phe Tyr Pro Ser Asp Ile Ala Val Glu Trp
        915                 920                 925
Glu Ser Asn Gly Gln Pro Glu Asn Asn Tyr Lys Thr Thr Pro Pro Val
    930                 935                 940
Leu Asp Ser Asp Gly Ser Phe Phe Leu Tyr Ser Lys Leu Thr Val Asp
945                 950                 955                 960
Lys Ser Arg Trp Gln Gln Gly Asn Val Phe Ser Cys Ser Val Met His
                965                 970                 975
Glu Ala Leu His Asn His Tyr Thr Gln Lys Ser Leu Ser Leu Ser Pro
            980                 985                 990
Gly Lys

<210> SEQ ID NO 2
<211> LENGTH: 991
<212> TYPE: PRT
<213> ORGANISM: Artificial Sequence
<220> FEATURE:
<223> OTHER INFORMATION: Chimeric Sequence for leader peptide/human
      scIL-12/hu51-4 heavy chain

<400> SEQUENCE: 2

Met Cys His Gln Gln Leu Val Ile Ser Trp Phe Ser Leu Val Phe Leu
1               5                   10                  15
Ala Ser Pro Leu Ile Trp Glu Leu Lys Lys Asp Val Tyr Val Val Glu
            20                  25                  30
Leu Asp Trp Tyr Pro Asp Ala Pro Gly Glu Met Val Val Leu Thr Cys
        35                  40                  45
Asp Thr Pro Glu Glu Asp Gly Ile Thr Trp Thr Leu Asp Gln Ser Ser
    50                  55                  60
Glu Val Leu Gly Ser Gly Lys Thr Leu Thr Ile Gln Val Lys Glu Phe
65                  70                  75                  80
Gly Asp Ala Gly Gln Tyr Thr Cys His Lys Gly Gly Glu Val Leu Ser
                85                  90                  95
His Ser Leu Leu Leu Leu His Lys Lys Glu Asp Gly Ile Trp Ser Thr
            100                 105                 110
Asp Ile Leu Lys Asp Gln Lys Glu Pro Lys Asn Lys Thr Phe Leu Arg
        115                 120                 125
Cys Glu Ala Lys Asn Tyr Ser Gly Arg Phe Thr Cys Trp Trp Leu Thr
    130                 135                 140
Thr Ile Ser Thr Asp Leu Thr Phe Ser Val Lys Ser Ser Arg Gly Ser
145                 150                 155                 160
Ser Asp Pro Gln Gly Val Thr Cys Gly Ala Ala Thr Leu Ser Ala Glu
                165                 170                 175
Arg Val Arg Gly Asp Asn Lys Glu Tyr Glu Tyr Ser Val Glu Cys Gln
            180                 185                 190
Glu Asp Ser Ala Cys Pro Ala Ala Glu Glu Ser Leu Pro Ile Glu Val
```

```
            195                 200                 205
Met Val Asp Ala Val His Lys Leu Lys Tyr Glu Asn Tyr Thr Ser Ser
    210                 215                 220

Phe Phe Ile Arg Asp Ile Ile Lys Pro Asp Pro Lys Asn Leu Gln
225                 230                 235                 240

Leu Lys Pro Leu Lys Asn Ser Arg Gln Val Glu Val Ser Trp Glu Tyr
                245                 250                 255

Pro Asp Thr Trp Ser Thr Pro His Ser Tyr Phe Ser Leu Thr Phe Cys
            260                 265                 270

Val Gln Val Gln Gly Lys Ser Lys Arg Glu Lys Lys Asp Arg Val Phe
        275                 280                 285

Thr Asp Lys Thr Ser Ala Thr Val Ile Cys Arg Lys Asn Ala Ser Ile
    290                 295                 300

Ser Val Arg Ala Gln Asp Arg Tyr Tyr Ser Ser Ser Trp Ser Glu Trp
305                 310                 315                 320

Ala Ser Val Pro Cys Ser Gly Gly Gly Ser Gly Gly Gly Gly Ser
                325                 330                 335

Gly Gly Gly Gly Ser Arg Asn Leu Pro Val Ala Thr Pro Asp Pro Gly
            340                 345                 350

Met Phe Pro Cys Leu His His Ser Gln Asn Leu Leu Arg Ala Val Ser
        355                 360                 365

Asn Met Leu Gln Lys Ala Arg Gln Thr Leu Glu Phe Tyr Pro Cys Thr
370                 375                 380

Ser Glu Glu Ile Asp His Glu Asp Ile Thr Lys Asp Lys Thr Ser Thr
385                 390                 395                 400

Val Glu Ala Cys Leu Pro Leu Glu Leu Thr Lys Asn Glu Ser Cys Leu
                405                 410                 415

Asn Ser Arg Glu Thr Ser Phe Ile Thr Asn Gly Ser Cys Leu Ala Ser
            420                 425                 430

Arg Lys Thr Ser Phe Met Met Ala Leu Cys Leu Ser Ser Ile Tyr Glu
        435                 440                 445

Asp Leu Lys Met Tyr Gln Val Glu Phe Lys Thr Met Asn Ala Lys Leu
    450                 455                 460

Leu Met Asp Pro Lys Arg Gln Ile Phe Leu Asp Gln Asn Met Leu Ala
465                 470                 475                 480

Val Ile Asp Glu Leu Met Gln Ala Leu Asn Phe Asn Ser Glu Thr Val
                485                 490                 495

Pro Gln Lys Ser Ser Leu Glu Glu Pro Asp Phe Tyr Lys Thr Lys Ile
            500                 505                 510

Lys Leu Cys Ile Leu Leu His Ala Phe Arg Ile Arg Ala Val Thr Ile
        515                 520                 525

Asp Arg Val Met Ser Tyr Leu Asn Ala Ser Leu Glu Gln Val Gln Leu
    530                 535                 540

Val Gln Ser Gly Ala Glu Val Lys Lys Pro Gly Ala Ser Val Lys Val
545                 550                 555                 560

Ser Cys Lys Ala Ser Gly Tyr Thr Phe Thr Arg Tyr Trp Met His Trp
                565                 570                 575

Val Arg Gln Ala Pro Gly Gln Gly Leu Glu Trp Ile Gly Ala Ile Tyr
            580                 585                 590

Pro Gly Asn Ser Asp Thr Ser Tyr Asn Gln Lys Phe Lys Gly Lys Ala
        595                 600                 605

Thr Ile Thr Ala Asp Thr Ser Thr Asn Thr Ala Tyr Met Glu Leu Ser
    610                 615                 620
```

```
Ser Leu Arg Ser Glu Asp Thr Ala Val Tyr Tyr Cys Ala Arg Gly Glu
625                 630                 635                 640

Glu Ile Gly Ser Arg Arg Trp Phe Ala Tyr Trp Gly Gln Gly Thr Leu
                645                 650                 655

Val Thr Val Ser Ser Ala Ser Thr Lys Gly Pro Ser Val Phe Pro Leu
            660                 665                 670

Ala Pro Ser Ser Lys Ser Thr Ser Gly Gly Thr Ala Ala Leu Gly Cys
        675                 680                 685

Leu Val Lys Asp Tyr Phe Pro Glu Pro Val Thr Val Ser Trp Asn Ser
    690                 695                 700

Gly Ala Leu Thr Ser Gly Val His Thr Phe Pro Ala Val Leu Gln Ser
705                 710                 715                 720

Ser Gly Leu Tyr Ser Leu Ser Ser Val Val Thr Val Pro Ser Ser Ser
                725                 730                 735

Leu Gly Thr Gln Thr Tyr Ile Cys Asn Val Asn His Lys Pro Ser Asn
            740                 745                 750

Thr Lys Val Asp Lys Lys Val Glu Pro Lys Ser Cys Asp Lys Thr His
        755                 760                 765

Thr Cys Pro Pro Cys Pro Ala Pro Glu Leu Leu Gly Gly Pro Ser Val
    770                 775                 780

Phe Leu Phe Pro Pro Lys Pro Lys Asp Thr Leu Met Ile Ser Arg Thr
785                 790                 795                 800

Pro Glu Val Thr Cys Val Val Val Asp Val Ser His Glu Asp Pro Glu
                805                 810                 815

Val Lys Phe Asn Trp Tyr Val Asp Gly Val Glu Val His Asn Ala Lys
            820                 825                 830

Thr Lys Pro Arg Glu Glu Gln Tyr Asn Ser Thr Tyr Arg Val Val Ser
        835                 840                 845

Val Leu Thr Val Leu His Gln Asp Trp Leu Asn Gly Lys Glu Tyr Lys
    850                 855                 860

Cys Lys Val Ser Asn Lys Ala Leu Pro Ala Pro Ile Glu Lys Thr Ile
865                 870                 875                 880

Ser Lys Ala Lys Gly Gln Pro Arg Glu Pro Gln Val Tyr Thr Leu Pro
                885                 890                 895

Pro Ser Arg Asp Glu Leu Thr Lys Asn Gln Val Ser Leu Thr Cys Leu
            900                 905                 910

Val Lys Gly Phe Tyr Pro Ser Asp Ile Ala Val Glu Trp Glu Ser Asn
        915                 920                 925

Gly Gln Pro Glu Asn Asn Tyr Lys Thr Thr Pro Pro Val Leu Asp Ser
    930                 935                 940

Asp Gly Ser Phe Phe Leu Tyr Ser Lys Leu Thr Val Asp Lys Ser Arg
945                 950                 955                 960

Trp Gln Gln Gly Asn Val Phe Ser Cys Ser Val Met His Glu Ala Leu
                965                 970                 975

His Asn His Tyr Thr Gln Lys Ser Leu Ser Leu Ser Pro Gly Lys
            980                 985                 990

<210> SEQ ID NO 3
<211> LENGTH: 236
<212> TYPE: PRT
<213> ORGANISM: Artificial Sequence
<220> FEATURE:
<223> OTHER INFORMATION: Chimeric Sequence for leader peptide/hu51-4
      light chain
```

```
<400> SEQUENCE: 3

Met Asp Phe Gln Val Gln Ile Phe Ser Phe Leu Leu Ile Ser Ala Ser
1               5                   10                  15

Val Ala Met Ser Arg Gly Glu Ile Val Leu Thr Gln Ser Pro Ala Thr
            20                  25              30

Leu Ser Leu Ser Pro Gly Glu Arg Ala Thr Leu Ser Cys Arg Ala Arg
        35              40              45

Gln Ser Ile Ser Asn Tyr Leu His Trp Tyr Gln Gln Lys Pro Gly Gln
    50              55                  60

Ala Pro Arg Leu Leu Ile Tyr Tyr Ala Ser Gln Ser Ile Ser Gly Ile
65              70              75                      80

Pro Asp Arg Phe Ser Gly Ser Gly Ser Gly Thr Asp Phe Thr Leu Thr
                85              90              95

Ile Ser Arg Leu Glu Pro Glu Asp Phe Ala Val Tyr Tyr Cys Gln Gln
                100             105             110

Ser Asn Ser Trp Pro Leu Thr Phe Gly Gln Gly Thr Lys Val Glu Ile
            115             120             125

Lys Arg Thr Val Ala Ala Pro Ser Val Phe Ile Phe Pro Pro Ser Asp
    130             135             140

Glu Gln Leu Lys Ser Gly Thr Ala Ser Val Val Cys Leu Leu Asn Asn
145             150             155             160

Phe Tyr Pro Arg Glu Ala Lys Val Gln Trp Lys Val Asp Asn Ala Leu
            165             170             175

Gln Ser Gly Asn Ser Gln Glu Ser Val Thr Glu Gln Asp Ser Lys Asp
            180             185             190

Ser Thr Tyr Ser Leu Ser Ser Thr Leu Thr Leu Ser Lys Ala Asp Tyr
        195             200             205

Glu Lys His Lys Val Tyr Ala Cys Glu Val Thr His Gln Gly Leu Ser
    210             215             220

Ser Pro Val Thr Lys Ser Phe Asn Arg Gly Glu Cys
225             230             235
```

TARGETED IL-12 TREATMENTS AND METHODS TO STIMULATE haNK AND NK92mi CELLS

This application claims priority to our U.S. provisional patent application with the Ser. No. 62/728,510, which was filed Sep. 7, 2018, which is incorporated by reference herein.

INCORPORATION BY REFERENCE

The instant application contains a Sequence Listing which has been submitted in ASCII format via EFS-Web and is hereby incorporated by reference in its entirety. Said ASCII copy was created on Jul. 18, 2018, is named 102719.0016PRO_ST25.txt, and is 19,610 bytes in size.

FIELD OF THE INVENTION

The field of the invention is cancer treatments and methods using natural killer cells and immune stimulatory cytokines, and especially activated NK cells and IL-12.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, cell-based cancer treatments with genetically modified NK cells have gained attention due to positive treatment outcomes, particularly where NK92 derivatives such as activated NK cells (aNK cells), genetically modified NK cells with high affinity CD16 receptors (haNK cells), or chimeric antigen receptors (taNK cells) were used. While such cell-based treatments are conceptually attractive, the tumor microenvironment and other patient-specific factors will often reduce their cytotoxic activity, and various attempts have been made to modulate cytotoxicity in NK92 cells.

Interleukin-2 (IL-2) and interleukin-12 (IL-12) cytokines elicit strong antitumor effects by stimulating unmodified immune cells, including T cells and natural killer (NK) cells. Although either cytokine stimulates the proliferation of T cells, the production of interferon-γ (IFN-γ) by NK cells, and ultimately the cytolytic activity, the magnitude, and the spectrum of stimulatory effects by IL-2 and IL-12 are different (see e.g., *J. Leukoc. Biol.* 58: 225-233; 1995). For example, while IL-2 is a stronger stimulator of proliferation and cytolytic activity, IL-12 is a stronger inducer of IFN-γ from unmodified NK cells and activated T cells. IFN-γ mRNA has increased stability in NK cells co-stimulated with IL-2 and IL-12 (see e.g., *Molecular and Cellular Biology*, March 2002, p. 1742-53). However, the IL-2 and IL-12 concentrations used in vitro may not necessarily reflect achievable or even desirable levels in vivo. Indeed, IL-2 systemic administration of IL-2 is associated with relatively high toxicity and capillary leak syndrome, while several deaths have been attributed to systemic administration of IL-12. In addition, the response of primary NK cells to various cytokines is not necessarily the same as the response of genetically modified NK92 cells.

Therefore, even though various compositions and methods are known to activate NK cells, there remains a need for compositions and methods to treat cancer using NK cells, especially where the NK cells are stimulated with IL-12 in a clinically safe manner.

SUMMARY OF THE INVENTION

Disclosed herein are various compositions and methods of NK cell based treatments. In particular, the present disclosure describes NK cells that express and intracellularly retain IL-2, in which the NK cells are stimulated with a chimeric protein that comprises a cancer cell targeting portion and an IL-12 portion. Advantageously, such chimeric protein has substantially reduced systemic toxicity and moreover beneficially induces IFN-γ secretion in a targeted manner. Unexpectedly, such chimeric proteins significantly enhance IFN-γ secretion in NK cells that express and intracellularly retain IL-2 as compared to native NK cells.

In one aspect of the inventive subject matter, the inventor contemplates a method of inducing IFNγ secretion in an NK cell that includes one step of providing an NK cell, wherein the NK cell is an IL-2 sensitized NK cell or a genetically modified NK cell that constitutively expresses IL-2; and another step of contacting the NK cell with a chimeric protein that comprises an IL-12 portion and a cancer cell targeting portion to induce interferon gamma (IFNγ) secretion by the NK cell.

In some embodiments, the IL-2 sensitized NK cell is an NK cell that was previously and constitutively exposed to IL-2 or an NK cell was that constitutively exposed to at least 100 IU/mL IL-2. In other embodiments, the genetically modified NK cell may also be an aNK cell, an autologous NK cell, or an NK cell derived in vitro from a precursor cell, while in still further embodiments the genetically modified NK cell constitutively expresses and intracellularly retains IL-2 (e.g., haNK cell or an NK92MI cell).

It is further contemplated that the IL-12 portion of the chimeric protein comprises an IL-12α chain and an IL-12β chain, but homodimers of IL-12α chain and other heterodimers are also deemed suitable. In some embodiments, the cancer cell targeting portion comprises an IgG antibody portion, a Fab portion, a F(ab')2 portion, a Fab2 portion, or an scFv portion. Most typically, the cancer cell targeting portion targets a necrosis marker (e.g., DNA, RNA, histone protein, etc.) or a cancer associated antigen or a cancer neoepitope to so afford site specificity with respect to IL-12 action. For example, suitable cancer cell targeting portions may comprise a hu51-4 antibody or portion thereof.

While not limiting to the inventive subject matter, it is contemplated that the step of contacting the NK cell with the chimeric protein is performed ex vivo and the NK cell is a haNK cell, or that the step of contacting the NK cell with the chimeric protein is performed in vivo and wherein the NK cell is a haNK cell or NK92MI cell.

Therefore, and viewed from a different perspective, the inventor also contemplates a method of treating cancer that includes a step of administering an NK cell to a patient, wherein the NK cell is an IL-2 sensitized NK cell or a genetically modified NK cell that constitutively expresses IL-2; and a further step of administering a chimeric protein that comprises an IL-12 portion and a cancer cell targeting portion to thereby induce interferon gamma (IFNγ) secretion by the NK cell.

As noted above, it is contemplated that the NK cell may be a genetically modified NK cell that constitutively expresses and intracellularly retains IL-2 (e.g., haNK cell or NK92MI cell), and/or that the IL-12 portion of the chimeric protein comprises an IL-12α chain and an IL-12β chain. In other examples, the cancer cell targeting portion may comprise an IgG antibody portion, a Fab portion, a F(ab')2 portion, a Fab2 portion, or an scFv portion, and it is generally preferred that the cancer cell targeting portion targets a necrosis marker (e.g., DNA, RNA, histone protein, etc.) or a cancer associated antigen or a cancer neoepitope. For example, the cancer cell targeting portion may comprise a hu51-4 antibody or portion thereof.

In further embodiments it is contemplated that the chimeric protein is administered at least 12 hours prior to administration of the NK cell, or that the chimeric protein is administered at least 12 hours after administration of the NK cell, or that the chimeric protein is contemporaneously administered with the NK cell. Among other options, it is also contemplated that the chimeric protein is bound to the NK cell.

In yet another aspect of the inventive subject matter, the inventor also contemplates a chimeric protein that comprises an IL-12 portion and a cancer cell targeting portion that targets a necrosis marker (e.g., DNA, RNA, histone protein, etc.), and/or that the cancer cell targeting portion comprises a hu51-4 antibody or portion thereof. In other embodiments, the cancer cell targeting portion includes an IgG antibody portion, a Fab portion, a F(ab')2 portion, a Fab2 portion, or an scFv portion.

For example, the IL-12 portion may be covalently coupled to the cancer cell targeting portion, and/or the IL-12 portion is covalently coupled to the cancer cell targeting portion via a peptide linker. Typically, but not necessarily, the IL-12 portion of the chimeric protein comprises an IL-12α chain and an IL-12β chain, and/or the cancer cell targeting portion comprises a hu51-4 antibody or portion thereof. Where desirable, the chimeric protein may be non-covalently bound to the CD16 receptor of an NK cell.

Consequently, the inventor also contemplates a pharmaceutical composition comprising the chimeric protein contemplated herein. Such pharmaceutical composition may further comprise an NK cell as described above. Thus, the inventor also contemplates a kit comprising (a) an NK cell, wherein the NK cell is an IL-2 sensitized NK cell or a genetically modified NK cell that constitutively expresses IL-2; and (b) a chimeric protein that comprises an IL-12 portion and a cancer cell targeting portion. With respect to the NK cell and the chimeric protein, the same considerations as provided above apply.

Viewed from a different perspective, the inventor therefore also contemplates use of a chimeric protein and an NK cell in the treatment of cancer, wherein the NK cell is an IL-2 sensitized NK cell or a genetically modified NK cell that constitutively expresses IL-2, and wherein the chimeric protein comprises an IL-12 portion and a cancer cell targeting portion that induces interferon gamma (IFNγ) secretion by the NK cell. With respect to the NK cells and/or the chimeric protein, the same considerations as noted above apply.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 4 shows sequences for exemplary chimeric proteins comprising an IL-12 portion.

DETAILED DESCRIPTION

Figure 1:
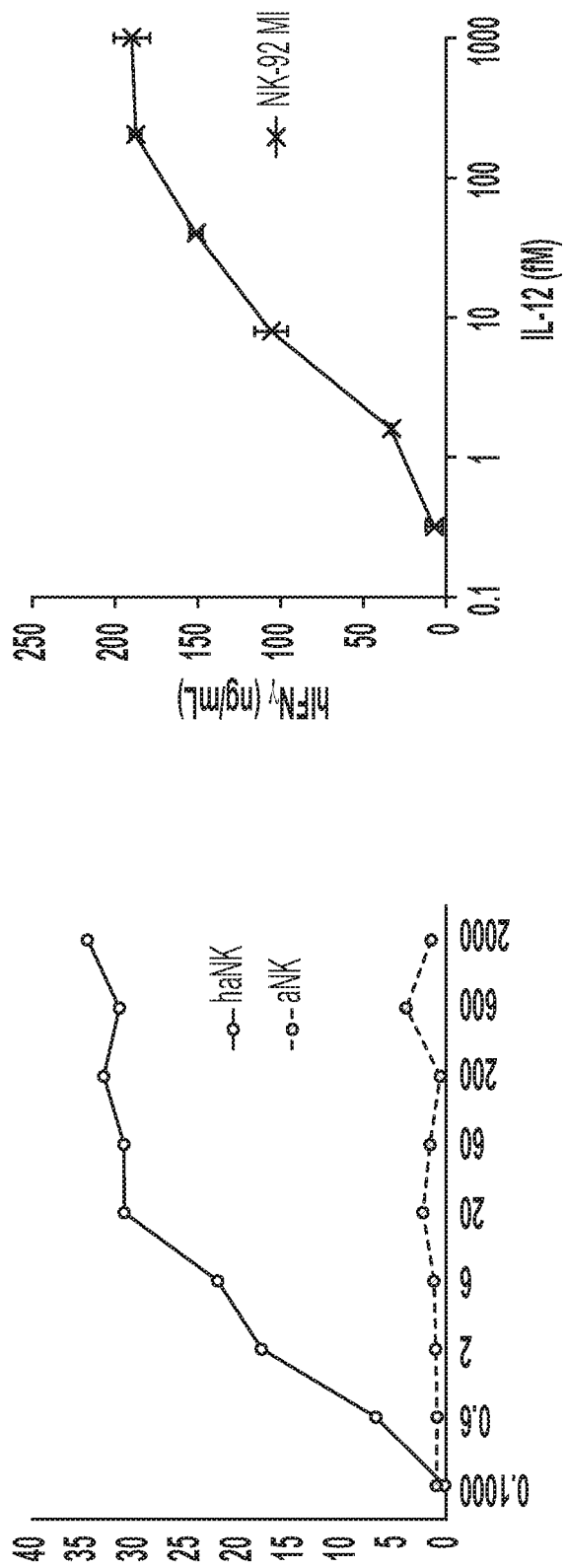
FIG. 1 shows exemplary graphs indicating that the tested NK cells require constitutive IL-2 expression/exposure for significant IL-12 mediated IFN-γ secretion.

The inventor has now discovered that selected chimeric molecules comprising an IL-12 portion can be used in an effective and targeted manner to induce IFNγ secretion in IL-2 sensitized NK cells or in genetically modified NK cells that constitutively express IL-2 to thereby promote cytotoxic NK cell activity in a target tissue. Advantageously, the chimeric molecules comprising the IL-12 portion help avoid toxicity otherwise encountered with systemically administered IL-12. Moreover, as the chimeric molecule also includes a cancer targeting moiety (e.g., targeting one or more necrosis markers), induction of IFNγ secretion by the NK cells can be rendered specific to the site of the cancer, and particularly to the hypoxic and/or necrotic tumor core. Therefore, due to the target specific IFNγ secretion, contemplated compositions and methods will increase antigen presentation and MHC-I/II expression of immune competent cells (and especially CD4+ and/or CD8+ T cells) in a tumor, and bias the immune response in the tumor towards a Th1 response.

Advantageously, use of the chimeric molecules presented herein not only avoids toxicity otherwise encountered with systemically administered IL-12, but also affords concentrated therapeutically effective quantities of IL-12 at the targeted tumor site. In addition, it should be appreciated that use of necrosis markers in the context presented herein will advantageously allow for a tumor antigen independent antigen spread in the tumor microenvironment as the chimeric molecule will indiscriminately target necrotic tissue rather than cancer or tumor associated antigens. In still further beneficial aspects, the chimeric molecules presented herein retain the biological activity of the IL-12 heterodimer as is discussed in more detail below.

In addition, it should be particularly recognized that various NK cells will fail to respond to IL-12, even where propagated with IL-2 supplied into the culture medium. Notably, however, the inventor has also discovered that when IL-2 is supplied to the same cells in a constitutive or continuous manner, the cells are sensitive to IL-12 signaling. The NK cells treated in this manner produce significant quantities of IFNγ and have increased cytotoxicity, presumably due to increased intracellular concentrations and/or less fluctuations in IL-2 quantities.

The terms 'constitutive exposure' or 'constitutively exposing' in conjunction with IL-2 as used herein means that biologically active IL-2 is supplied or produced in a continuous (or semi-continuous) manner such that variations in biologically active IL-2 concentration at or in the cell (or IL-2 stimulation) will vary by no more than 20% over 48 hours. Therefore, in some embodiments, variations in biologically active IL-2 concentration at or in the cell (or IL-2 stimulation) will vary by no more than 15% over 48 hours, or no more than 10% over 48 hours, or no more than 7% over 48 hours, or no more than 5% over 48 hours, or no more than 1% over 48 hours. Likewise, the terms "constitutive expression" or "constitutively expressing" in conjunction with IL-2 as used herein refers to (recombinant) expression of IL-2 within a cell in a continuous fashion from a constitutive promoter (i.e., without the need for induction). Most typically, such expression of IL-2 within a cell will be achieved by use of an endoplasmic retention sequence that is fused to the IL-2 to reduce or even entirely avoid secretion form the cell expressing such modified IL-2.

While not limiting to the inventive subject matter and without being bound by theory, constitutive exposure to IL-2 is hypothesized to resemble more closely the exposure of NK cells to IL-2 in a natural setting, leading to durable sensitivity to IL-12 and IFNγ secretion triggered by exposure to IL-12. In contrast, intermittent exposure of NK-92 cells to IL-2—as is the case in customary NK-92 cell culture, where culture media are renewed every two to three days—may lead to inactivation and/or degradation of biologically active IL-2, possibly due to binding by serum proteins or proteolysis by serum proteases of the culture media. Consequently, and without wishing to be bound by any theory or hypothesis, the inventor believes that customary NK-92 cell culture conditions promote intermittent or 'pulsed' IL-2 signaling which supports growth of NK-92 cells but fails to support cell signaling to render the NK-92 cells sensitive to IL-12 and IL-12 dependent IFNγ secretion as well as increased (as compared to non-IL-12 stimulated cells) expression of NKG2D.

With respect to contemplated chimeric proteins it is generally contemplated that all chimeric proteins that include at least a biologically active IL-12 portion are suitable. Moreover, it is generally preferred that the chimeric protein also includes a portion that extends serum half life time, that reduces systemic toxicity, and/or that allows target specific delivery and/or accumulation of IL-12 at a desired site. Consequently, with regard to the non-IL-12 portion of the chimeric protein, suitable non-IL-12 portions include various serum proteins and portions thereof, and particularly albumin, lactoferrin, and various globulins. Therefore, one preferred non-IL-12 portion comprises an antibody or fragment thereof. As will be readily appreciated, use of antibodies or fragments thereof will beneficially allow targeting while also extending the stability and persistence of the chimeric protein in blood. For example, the non-IL-12 portion may be a heavy chain of an antibody, a light chain of an antibody (or portion thereof), or a scFv.

While any binding specificity for such antibody or fragment thereof is generally deemed suitable, especially preferred antibodies will specifically bind to an antigen of a tumor cell. For example, suitable antibodies may bind to a tumor associated antigen, a tumor specific antigen, or a patient and tumor specific neoantigen (neoepitope). Therefore, the non-IL-12 portion is most preferably also used to deliver and retain the IL-12 at the site of a tumor to concentrate the biological effect of the IL-12 to the target site. Furthermore, it should be recognized that all sources of antibodies are deemed suitable, including human antibodies and all isoforms, non-human mammalian forms, humanized forms, and synthetic antibodies. Where the non-IL-12 portion is not an antibody, tumor selectivity or preference may nevertheless be achieved via albumin that is preferentially taken up into tumor cells from the neovasculature via gp60 mediated transcytosis.

With respect to the IL-12 portion, it should be noted that IL-12 is a heterodimer and that the IL-12 portion in the chimeric protein may be a single chain form of IL-12 (i.e., scIL-12) or a single subunit (i.e., IL-12α subunit (p35) and IL-12β subunit (p40)) or active portion thereof. With respect to the source of the IL-12, it is generally preferred that the source be human IL-12. However, various other non-human (preferably mammalian) IL-12 forms are also expressly contemplated herein. Moreover, it should be appreciated that splice variants and mutants are also appropriate, so long as such forms exhibit at least some biological activity (e.g., induce IFNγ secretion in haNK cells as described herein).

Suitable IL-12 protein sequences include human sequences, which may form a disulfide linked heterodimer formed from IL-12α subunit (p35) and IL-12β subunit (p40) or which may be covalently linked together via a flexible peptide linker as described in more detail below. Among other suitable sequences, IL-12 sequences include publically available protein sequence (e.g., P29460 and P29459 at UniProt), and all natural and synthetic variants thereof, including truncated forms, splice variants, and mutant forms. Likewise, DNA and RNA sequences encoding IL-12 are known in the art and suitable sequences include those at Genbank (accession number AC010370 for genomic sequence and M65271 for mRNA of IL-12α subunit; accession number AF512686 for genomic sequence and M65290 for mRNA of IL-12β subunit). Moreover, it should be appreciated that other non-human, preferably mammalian sequences, are also deemed suitable for use herein.

Heterodimers of IL-12α subunit and IL-12β subunit may be formed by non-covalent association, or via a flexible peptide linker such as a G4S linker to form a single chain IL-12 molecule. Furthermore, the chimeric proteins may also include addressing or leader sequences, linkers, tags, and/or flag for quantification and/or simplified purification. The proper choice will depend, at least in part, on the particular choice of production system, as is well known in the art.

It is still further contemplated that the manner of production of a chimeric protein with the IL-12 portion and the non-IL-12 portion may vary considerably, and will include covalent coupling of the two portions heavy chain as well as non-covalent coupling. For example, a necrosis targeting antibody hu51-4 was used as a fusion partner with a single chain IL-12 (scIL-12) as is described in more detail below. Likewise, NHS-IL12 is a chimeric construct that includes two molecules of IL-12 that are fused to a tumor necrosis-targeting human IgG1 (NHS76). The addition of the human IgG1 moiety resulted in a longer plasma half-life of NHS-IL12 than recombinant IL-12, and a selective targeting to murine tumors in vivo. Data from both in vitro assays using human PBMCs and in vivo primate studies showed that IFNγ production by immune cells was attenuated following treatment with the immunocytokine, suggesting an improved toxicity profile than seen with recombinant IL-12 alone. NHS-IL12 was also superior to recombinant IL-12 when evaluated as an anti-tumor agent in three murine tumor models (see e.g., *Oncotarget* 2014 Apr. 15; 5(7):1869-84).

As will be readily appreciated, such antibody-cytokine conjugates may be prepared by chemical conjugation using cleavable (e.g., via disulfide bond or hydrazone, or proteolytic site, etc.) or non-cleavable linkers (e.g., via maleimide-modified PEG). Alternatively, the conjugation may also be done using recombinant cloning in which the N- or C-terminus of the heavy or light chain (or fragment thereof) is modified to also encode in frame a linker portion and IL-12 as is also shown in more detail below. Thus, chimeric recombinant proteins can be prepared that have an antibody portion that preferably binds to a component of a tumor cell, a linker, and an IL-12 portion. Notably, exemplary antibody-drug conjugates with IL-12 retained significant activity as is shown in more detail below.

One exemplary fusion protein may therefore include a chimeric protein having a leader peptide portion, a murine scIL-12 portion in normal type font (G₄S linker in bold type), and a hu51-4 antibody heavy chain portion as shown below in SEQ ID NO:1, in which the italicized sequence denotes the leader peptide portion, and in which the underlined sequence denotes the hu51-4 antibody heavy chain portion.

[SEQ ID NO: 1]
*MCHQQLVISWFSLVFLASPLM*WELEKDVYVVEVDWTPDAPGETVNLTCDT

PEEDDITWTSDQRHGVIGSGKTLTITVKEFLDAGQYTCHKGGETLSHSHL

LLHKKENGIWSTEILKNFKNKTFLKCEAPNYSGRFTCSWLVQRNMDLKFN

IKSSSSSPDSRAVTCGMASLSAEKVTLDQRDYEKYSVSCQEDVTCPTAEE

TLPIELALEARQQNKYENYSTSFFIRDIIKPDPPKNLQMKPLKNSQVEVS

WEYPDSWSTPHSYFSLKFFVRIQRKKEKMKETEEGCNQKGAFLVEKTSTE

VQCKGGNVCVQAQDRYYNSSCSKWACVPCRVRSGGGGSGGGGSGGGGSRV

IPVSGPARCLSQSRNLLKTTDDMVKTAREKLKHYSCTAEDIDHKDITRDQ

TSTLKTCLPLELHKNESCLATRETSSTTRGSCLPPQKTSLMMTLCLGSIY

EDLKMYQTEFQAINAALQNHNHQQIILDKGMLVAIDELMQSLNHNGETLR

QKPPVGEADPYRVKMKLCILLHAFSTRVVTINRVMGYLSSA<u>LEQVQLVQS</u>

<u>GAEVKKPGASVKVSCKASGYTFTRYWMHWVRQAPGQGLEWIGAIYPGNSD</u>

<u>TSYNQKFKGKATITADTSTNTAYMELSSLRSEDTAVYYCARGEEIGSRRW</u>

<u>FAYWGQGTLVTVSSASTKGPSVFPLAPSSKSTSGGTAALGCLVKDYFPEP</u>

<u>VTVSWNSGALTSGVHTFPAVLQSSGLYSLSSVVTVPSSSLGTQTYICNVN</u>

<u>HKPSNTKVDKKVEPKSCDKTHTCPPCPAPELLGGPSVFLFPPKPKDTLMI</u>

<u>SRTPEVTCVVVDVSHEDPEVKFNWYVDGVEVHNAKTKPREEQYNSTYRVV</u>

<u>SVLTVLHQDWLNGKEYKCKVSNKALPAPIEKTISKAKGQPREPQVYTLPP</u>

<u>SRDELTKNQVSLTCLVKGFYPSDIAVEWESNGQPENNYKTTPPVLDSDGS</u>

<u>FFLYSKLTVDKSRWQQGNVFSCSVMHEALHNHYTQKSLSLSPGK.</u>

Another exemplary fusion protein may include a leader peptide portion, a human scIL-12 portion in normal type font (G₄S linker in bold type), and a hu51-4 antibody heavy chain portion as shown below in SEQ ID NO:2, in which the italicized sequence denotes the leader peptide portion, and in which the underlined sequence denotes the hu51-4 antibody heavy chain portion.

[SEQ ID NO: 2]
*MCHQQLVISWFSLVFLASPLI*WELKKDVYVVELDWYPDAPGEMVVLTCDT

PEEDGITWTLDQSSEVLGSGKTLTIQVKEFGDAGQYTCHKGGEVLSHSLL

LLHKKEDGIWSTDILKDQKEPKNKTFLRCEAKNYSGRFTCWWLTTISTDL

TFSVKSSRGSSDPQGVTCGAATLSAERVRGDNKEYEYSVECQEDSACPAA

EESLPIEVMVDAVHKLKYENYTSSFFIRDIIKPDPPKNLQLKPLKNSRQV

EVSWEYPDTWSTPHSYFSLTFCVQVQGKSKREKKDRVFTDKTSATVICRK

NASISVRAQDRYYSSSWSEWASVPCSGGGGSGGGGSGGGGSRNLPVATPD

PGMFPCLHHSQNLLRAVSNMLQKARQTLEFYPCTSEEIDHEDITKDKTST

VEACLPLELTKNESCLNSRETSFITNGSCLASRKTSFMMALCLSSIYEDL

KMYQVEFKTMNAKLLMDPKRQIFLDQNMLAVIDELMQALNFNSETVPQKS

SLEEPDFYKTKIKLCILLHAFRIRAVTIDRVMSYLNAS<u>LEQVQLVQSGAE</u>

<u>VKKPGASVKVSCKASGYTFTRYWMHWVRQAPGQGLEWIGAIYPGNSDTSY</u>

<u>NQKFKGKATITADTSTNTAYMELSSLRSEDTAVYYCARGEEIGSRRWFAY</u>

<u>WGQGTLVTVSSASTKGPSVFPLAPSSKSTSGGTAALGCLVKDYFPEPVTV</u>

<u>SWNSGALTSGVHTFPAVLQSSGLYSLSSVVTVPSSSLGTQTYICNVNHKP</u>

<u>SNTKVDKKVEPKSCDKTHTCPPCPAPELLGGPSVFLFPPKPKDTLMISRT</u>

<u>PEVTCVVVDVSHEDPEVKFNWYVDGVEVHNAKTKPREEQYNSTYRVVSVL</u>

<u>TVLHQDWLNGKEYKCKVSNKALPAPIEKTISKAKGQPREPQVYTLPPSRD</u>

<u>ELTKNQVSLTCLVKGFYPSDIAVEWESNGQPENNYKTTPPVLDSDGSFFL</u>

<u>YSKLTVDKSRWQQGNVFSCSVMHEALHNHYTQKSLSLSPGK.</u>

Still another exemplary protein includes a leader peptide portion and a hu51-4 antibody light chain portion as shown below in SEQ ID NO:3, in which the italicized sequence denotes the leader peptide portion, and in which the underlined sequence denotes the hu51-4 antibody light chain portion.

[SEQ ID NO: 3]
*MDFQVQIFSFLLISASVAMSRGE*<u>IVLTQSPATLSLSPGERATLSCRARQS</u>

<u>ISNYLHWYQQKPGQAPRLLIYYASQSISGIPDRFSGSGSGTDFTLTISRL</u>

<u>EPEDFAVYYCQQSNSWPLTFGQGTKVEIKRTVAAPSVFIFPPSDEQLKSG</u>

<u>TASVVCLLNNFYPREAKVQWKVDNALQSGNSQESVTEQDSKDSTYSLSST</u>

<u>LTLSKADYEKHKVYACEVTHQGLSSPVTKSFNRGEC.</u>

With respect to NK cells, it is generally contemplated that preferred NK cells are IL-2 sensitized NK cells or genetically modified NK cells that constitutively expresses IL-2. In this context, it should be noted that IL-2 sensitized cells are cells that were subjected to constitutive exposure with IL-2 as noted above.

While constitutive exposure can be done by continuous exposure and/or replenishment of IL-2 to the culture medium as described herein, constitutive exposure of NK/NK92 cells and their derivatives to IL-2 is more preferably achieved by intracellular expression of recombinant IL-2 in the respective cells. Typically, intracellular expression is driven from a constitutively active promoter to achieve constant expression levels, and is expressed in a form that is not secreted (i.e., lacks export signal sequence, and may include an endoplasmic or cytoplasmic retention sequence). Such intracellular expression is believed to provide the same functional impact to the cell as constitutive exposure to externally provided IL-2. Indeed, as is shown in more detail below, the inventor discovered that where NK92 cells or derivatives were genetically engineered to express and intracellularly retain IL-2, the cells were unexpectedly sensitized to IL-12 stimulation as measured by IFNγ secretion and/or increased expression of NKG2D. As will be readily appreciated, recombinant expression and intracellular retention of IL-2 can be done in numerous manners, and all of such methods are deemed suitable for use herein (see e.g., *Oncotarget* 2016 Dec. 27; 7(52): 86359-86373 or *Exp Hematol.* 2005 February; 33(2):159-64). Among other benefits, it should be noted that such recombinant cells can be administered to a patient in vivo without the need to administer to the same patient IL-2. Such modified cells will be sensitized to IL-12 to secrete IFNγ upon IL-12 stimulation. Indeed, sensitization by constitutive exposure (external or internal) to IL-2 provided substantial quantities of IFNγ that is thought to provide a therapeutic effect in the context of concomitant immune therapy, particularly as NKG2D expression in such stimulated cells was also significantly increased.

For example, genetically engineered NK cells may be NK-92 derivatives modified to express the high-affinity Fcγ receptor (CD16). Sequences for high-affinity variants of the Fcγ receptor are well known in the art (see e.g., *Blood* 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor), and such modified cells may also be commercially obtained from NantKwest as haNK cells ('high-affinity natural killer cells). Alternatively, NK92MI cells have been reported (see e.g., *Hum Gene Ther.* 1999 May 20; 10(8):1359-73 or U.S. Pat. No. 8,034,332) to express and retain IL-2 intracellularly and are commercially available from ATCC.

In still further contemplated aspects, and with respect to NK cells it is contemplated that all NK cells are deemed suitable for use herein so long as such cells are constitutively exposed to IL-2 or intracellularly express (and retain) IL-2 as described above. Thus suitable alternative NK cells include autologous NK cells from a patient (e.g., isolated from whole blood, or cultivated from precursor or stem cells using methods known in the art), and various allogenic NK cells. However, in preferred aspects of the inventive subject matter, the NK cells are genetically engineered to achieve one or more desirable traits, and particularly include NK-92 cells and derivatives thereof. For example, suitable genetically engineered NK cell include NK-92 derivatives that are modified to have reduced or abolished expression of at least one killer cell immunoglobulin-like receptor (KIR), which will render such cells constitutively activated (via lack of or reduced inhibition).

Therefore, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and/or KIR3DS1. Such modified cells may be prepared using protocols well known in the art. Alternatively, such cells may also be commercially obtained from NantKwest as aNK cells ('activated natural killer cells).

NK-92 cells exhibit an unusual receptor expression profile, expressing a relatively large number of activating (e.g., NKp30, NKp46, 2B4, NKGD, CD28) receptors. Conversely, NK-92 cells also express few inhibitory receptors (e.g., NKGA/B, low levels of KIR2DL4, ILT-2), and lack most of the killer inhibitory receptors (KIRs) clonally expressed on normal NK cells. In addition, NK-92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK-92 cells also express other molecules implicated immune effector cell regulation (CD80, CD86, CD40L, TRANCE) whose relevance in NK killing is unclear.

Therefore, the inventor contemplates that NK-92 cells and derivatives thereof can be sensitized to IL-12 and exhibit an IL-12 dependent IFNγ secretion phenotype by constitutively exposing the cells to IL-2. For example, in one embodiment constitutive exposure can be performed by continuous or semi-continuous addition of IL-2 to a culture medium to thereby maintain the concentration of biologically active IL-2 substantially constant. Therefore, it is contemplated that the concentration of biologically active IL-2 in the medium varies over 48 hours by no more than 15%, or by no more than 10%, or by no more than 7%, or by no more than 5%, or by no more than 3%. Biological activity of IL-2 can be quantified using known procedures, e.g., using a CTLL-2 cell proliferation assay (*J Immunol Methods.* 2009 Aug. 31; 348(1-2): 83-94).

Continuous or semi-continuous addition of IL-2 can be done in numerous manners, including use of a peristaltic pump or metered injector. Alternatively, and in less preferred aspects, continuous or semi-continuous addition of IL-2 can be done by media renewal in a frequent fashion (e.g., every two hours, every four hours, every eight hours, etc.). Where multiple or continuous additions are not preferred, the inventor also contemplates that the constitutive exposure can also be achieved using formulations that release IL-2 in a relatively slow manner. For example, delayed release of IL-2 (or increased stability against protein binding and/or protease digest) can be done by pegylation of IL-2 as is known from NKTR-214 (Nektar Therapeutics; 455 Mission Bay Blvd South; San Francisco, CA 94158). Here, pegylated IL-2 is believed to be a prodrug form of biologically active IL-2 that releases PEG chains over time to produce biologically active IL-2 (*PLoS One.* 2017 Jul. 5; 12(7):e0179431). Advantageously, such pegylated IL-2 can be systemically administered and as such allows for constitutive exposure of NK/NK92 cells and their derivatives to IL-2 in vivo while at the same time systemic side effects of IL-2 are reduced, or even entirely avoided. Continuous exposure advantageously is performed for at least 6 hours, or at least 12 hours, or at least 24 hours, or at least 36 hours, or at least 48 hours.

Alternatively, or additionally, it should be noted that constitutive exposure can also be achieved using antibody conjugated IL-2 as such conjugates have shown increased stability, presumably due to decreased binding to serum proteins and decreased proteolysis by serum proteases. Once more, such antibody-drug conjugates will advantageously be administrable to a patient in vivo. In this embodiment, however (and in contrast to NKTR-214), delivery of IL-2 and with that activation of NK cells, is possible with high specificity and selectivity as far as location is concerned. For example, such antibody-drug conjugates may target tumor markers that are patient and tumor specific (i.e., tumor neoepitopes), cancer associated, cancer specific, or specific to necrotic tissue commonly found in a tumor microenvironment. Of course, it should be appreciated that the antibody portion in such antibody-drug conjugates may be a full IgG antibody, or any suitable fragment thereof (e.g., scFv, Fab, Fab', F(ab')$_2$, etc.).

Regardless of the particular form of IL-2 it is generally contemplated that constitutive exposure of NK/NK92 cells and their derivatives to IL-2 (and modified forms of IL-2) will be at a concentration of between about 10-50 IU/mL, or between about 50-150 IU/mL, or between about 150-300 IU/mL, or between about 300-500 IU/mL, or between about 500-1000 IU/mL, or even higher (as determined by CTLL-2 proliferation assay). Moreover, it is generally contemplated that the IL-2 concentration remains substantially constant over at least a limited period of time. For example, it is typically preferred that the concentration of the biologically active IL-2 fluctuates less than 25%, or less than 20%, or less than 15%, or less than 10%, or less than 7%, or less than 5%, or less than 3% as measured in % change of IU/mL over a period of 72 hours, or over a period of 60 hours, or over a period of 48 hours, or over a period of 36 hours, or over a period of 24 hours, or over a period of 18 hours. Thus, viewed from a different perspective, suitable concentration of the biologically active IL-2 will be maintained throughout the entire cell culture between 50-70 IU/mL, or between 70-100 IU/mL, or between 100-120 IU/mL, or between 120-150 IU/mL, or between 150-200 IU/mL, or between 200-230 IU/mL, or between 230-250 IU/mL, or between 250-280 IU/mL, or higher.

In yet a further aspect of the inventive subject matter, the genetically engineered NK cell may also be genetically engineered to express a chimeric T-cell receptor. In especially preferred aspects, the chimeric T-cell receptor will have a scFv portion or other ectodomain with binding specificity against a tumor associated antigen, a tumor specific antigen, and a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells').

Where the cells are engineered to have affinity towards a cancer associated antigen or antibody with specificity towards a cancer associated antigen (e.g., via expression of a CAR), it is contemplated that all known cancer associated antigens are considered appropriate for use. For example, cancer associated antigens include CEA, MUC-1, CYPB1, etc. Likewise, where the cells are engineered to have affinity towards a cancer specific antigen or antibody with specificity towards a cancer specific antigen, it is contemplated that all known cancer specific antigens are considered appropriate for use. For example, cancer specific antigens include PSA, Her-2, PSA, brachyury, etc. Where the cells are engineered to have affinity towards a cancer neoepitope or antibody with specificity towards a cancer neoepitope, it is contemplated that all known manners of identifying neoepitopes will lead to suitable targets. For example, neoepitopes may be identified from a patient tumor in a first step by whole genome analysis of a tumor biopsy (or lymph biopsy or biopsy of a metastatic site) and matched normal tissue (i.e., non-diseased tissue from the same patient) via synchronous comparison of the so obtained omics information. The identified neoepitopes can then be further filtered for a match to the patient's HLA type to increase likelihood of antigen presentation of the neoepitope. Most preferably, such matching can be done in silico. In addition, all NK cells contemplated herein may also be genetically modified to express non-secreted IL-2 (e.g., retained in the ER compartment).

Therefore, in yet another aspect of the inventive subject matter, thusly stimulated NK cells as described herein may be used in a pharmaceutical composition or kit, typically formulated as a sterile injectable composition with between $10^4$-$10^{11}$ cells, and more typically $10^5$-$10^9$ cells per dosage unit. Where desirable, these cells may be irradiated at a suitable radiation dosage to prevent further propagation after administration. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection into the tumor, infusion, oral delivery, topical delivery, etc.). Additionally, or alternatively, contemplated pharmaceutical compositions and kits may include a chimeric protein that comprises an IL-12 portion and a cancer cell targeting portion as described herein.

Therefore, the inventor especially contemplates a method of treating cancer in which constitutively stimulated natural killer cells and chimeric protein contemplated herein are co-administered. As will be readily appreciated, such administration may follow various regimens. For example, where the NK cell includes a high-affinity CD16 receptor (e.g., haNK cells), the chimeric protein may be coupled to the NK cell via the receptor. On the other hand, for example, where the NK cell is an autologous NK cell, the NK cells may be stimulated by constitutive exposure to IL-2 as described herein and then be separately from the chimeric protein (co-)administered to the patient. Thus, the chimeric protein may be administered first, and after 12-24 hours or more, followed by administration of the stimulated NK cells. On the other hand, where a patient has already received a transfusion with NK cells that constitutively express IL-2 (e.g., haNK cells, NK92MI cells), the chimeric protein may be administered after treatment with the NK cells.

Furthermore, as contemplated methods are also thought to increase NKD2D surface expression on various cells in addition to IFNγ secretion, and especially immune competent cells such as NK cells, CD8$^+$, and CD4$^+$ T-cells, it is further contemplated that treatments may also include one or more steps that augment or trigger NKG2D ligand expression and presentation. For example, such steps include low dose chemotherapy and/or low dose radiation therapy, typically performed at dosages that are equal or less than 50%, equal or less than 30%, equal or less than 20%, or equal or less than 10% of the maximum tolerated dose. Moreover, such low dose treatment will preferably be performed in a metronomic fashion, for example, on alternating days, or every third day, or once weekly for several weeks, etc.

Further Embodiments

Embodiment 1. A method of inducing IFNγ secretion in an NK cell, comprising: contacting the NK cell with a chimeric protein that comprises an IL-12 portion and a cancer cell targeting portion to induce interferon gamma (IFNγ) secretion by the NK cell, wherein the NK cell is an IL-2 sensitized NK cell or a genetically modified NK cell that constitutively expresses IL-2.

Embodiment 2. The method of Embodiment 1, wherein the IL-2 sensitized NK cell is an NK cell that was previously and constitutively exposed to IL-2, preferably at least 100 IU/mL IL-2.

Embodiment 3. The method of Embodiment 1 or 2, wherein any one or more of the following is true:
the genetically modified NK cell is an aNK cell, an autologous NK cell, or an NK cell derived in vitro from a precursor cell;
the genetically modified NK cell constitutively expresses and intracellularly retains IL-2;
the genetically modified NK cell is a haNK cell or an NK92MI cell; and
the IL-12 portion of the chimeric protein comprises an IL-12α chain and an IL-12β chain.

Embodiment 4. The method of any one of the previous Embodiments, wherein the cancer cell targeting portion targets a necrosis marker or a cancer associated antigen or a cancer neoepitope, and wherein the necrosis marker is preferably a DNA, an RNA, or a histone protein, and wherein the cancer cell targeting portion preferably comprises hu51-4 antibody or a portion thereof.

Embodiment 5. The method of any one of the previous Embodiments, wherein the chimeric protein comprises SEQ ID NO:1 or SEQ ID NO:2, and optionally SEQ ID NO:3.

Embodiment 6. The method of any one of the previous Embodiments, wherein any one or more of the following is true:
the step of contacting the NK cell with the chimeric protein is performed ex vivo, and the NK cell is a haNK cell; and
the step of contacting the NK cell with the chimeric protein is performed in vivo, and the NK cell is a haNK cell or NK92MI cell.

Embodiment 7. A composition for use in treating cancer in a subject in need thereof, the composition comprising and NK cell and a chimeric protein,
wherein the NK cell is an IL-2 sensitized NK cell or a genetically modified NK cell that constitutively expresses IL-2; and
wherein the chimeric protein comprises an IL-12 portion and a cancer cell targeting portion to thereby induce interferon gamma (IFNγ) secretion from the NK cell.

Embodiment 8. The composition of Embodiment 7, wherein the NK cell is a genetically modified NK cell that constitutively expresses and intracellularly retains IL-2, and wherein the NK cell is preferably a haNK cell or an NK92MI cell.

Embodiment 9. The composition of Embodiment 7 or 8, wherein any one or more of the following is true:
the IL-12 portion of the chimeric protein comprises an IL-12α chain and an IL-12β chain;
the cancer cell targeting portion comprises an IgG antibody portion, a Fab portion, a F(ab')$_2$ portion, a Fab$_2$ portion, or an scFv portion;
the cancer cell targeting portion targets a necrosis marker or a cancer associated antigen or a cancer neoepitope;
the necrosis marker is a DNA, an RNA, or a histone protein;
the cancer cell targeting portion comprises a hu51-4 antibody or portion thereof;
the chimeric protein comprises SEQ ID NO:1 or SEQ ID NO:2, and optionally SEQ ID NO:3; and
the chimeric protein is bound to the NK cell.

Embodiment 10. A chimeric protein that comprises an IL-12 portion and a cancer cell targeting portion that targets a necrosis marker, and optionally wherein any one or more of the following is true:
the necrosis marker is a DNA, an RNA, or a histone protein;
the cancer cell targeting portion comprises a hu51-4 antibody or portion thereof;
the IL-12 portion of the chimeric protein comprises an IL-12α chain and an IL-12β chain;
the chimeric protein comprises SEQ ID NO:1 and optionally SEQ ID NO:3;
the chimeric protein comprises SEQ ID NO:2 and optionally SEQ ID NO:3 and
the cancer cell targeting portion comprises an IgG antibody portion, a Fab portion, a F(ab')$_2$ portion, a Fab$_2$ portion, or an scFv portion.

Embodiment 11. The chimeric protein of Embodiment 10, wherein the IL-12 portion is covalently coupled to the cancer cell targeting portion, and optionally wherein the IL-12 portion is covalently coupled to the cancer cell targeting portion via a peptide linker.

Embodiment 12. The chimeric protein of Embodiment 10 or 11, wherein the chimeric protein is bound to CD16 of an NK cell.

Embodiment 13. A pharmaceutical composition comprising the chimeric protein of any one of Embodiments 10-12.

Embodiment 14. The pharmaceutical composition of Embodiment 13, wherein the composition further comprises an NK cell, wherein the NK cell is an IL-2 sensitized NK cell or a genetically modified NK cell that constitutively expresses IL-2, and optionally wherein any one or more of the following is true:
the NK cell is a haNK cell;
the NK cell is an NK92MI cell; and
the chimeric protein is bound to CD16 of an NK cell.

Embodiment 15. A chimeric antibody comprising a chimeric heavy chain that includes a scIL-12 portion and antigen binding portion that binds a cell death-exposed antigen, and optionally wherein any one or more of the following is true:
the scIL-12 comprises an IL-12α subunit linked by a peptide linker to an IL-12β subunit;
the antibody comprises SEQ ID NO:1 and optionally SEQ ID NO:3; and
the antibody comprises SEQ ID NO:2 and optionally SEQ ID NO:3.

Examples

To investigate the influence of constitutive exposure of NK cells to IL-2, three NK92 derivatives, aNK cells, haNK cells (commercially available from NantKwest), and NK92MI cells (commercially available from ATCC) were exposed to IL-12. The left panel of FIG. 1 comparatively depicts the data for aNK cells without constitutive IL-2 exposure and haNK cells with constitutive IL-2 exposure, while the right panel depicts NK92 derivatives that included stable integration of an IL-2 expression cassette (not expressing the high affinity CD16 variant). As can be taken from these results, the modified NK cells were not only responsive to IL-12 signaling to secrete IFNγ, but secreted unexpected high quantities of IFNγ (peaking near 200 ng/mL).

More particularly, NK-92 cells were previously transfected with human IL-2 cDNA in a retroviral MFG-hIL-2 vector by particle-mediated gene transfer. The transfection was stable. NK-92 and this derivative cell line NK-92MI had the following characteristics: surface marker positive for CD2, CD7, CD11a, CD28, CD45, CD54 and CD56 bright; surface marker negative for CD1, CD3, CD4, CD5, CD8, CD10, CD14, CD16, CD19, CD20, CD23, CD34 and HLA-DR. Cells were grown following standard protocol. IFNγ was measured using conventional ELISA methods well known in the art.

Figure 2:
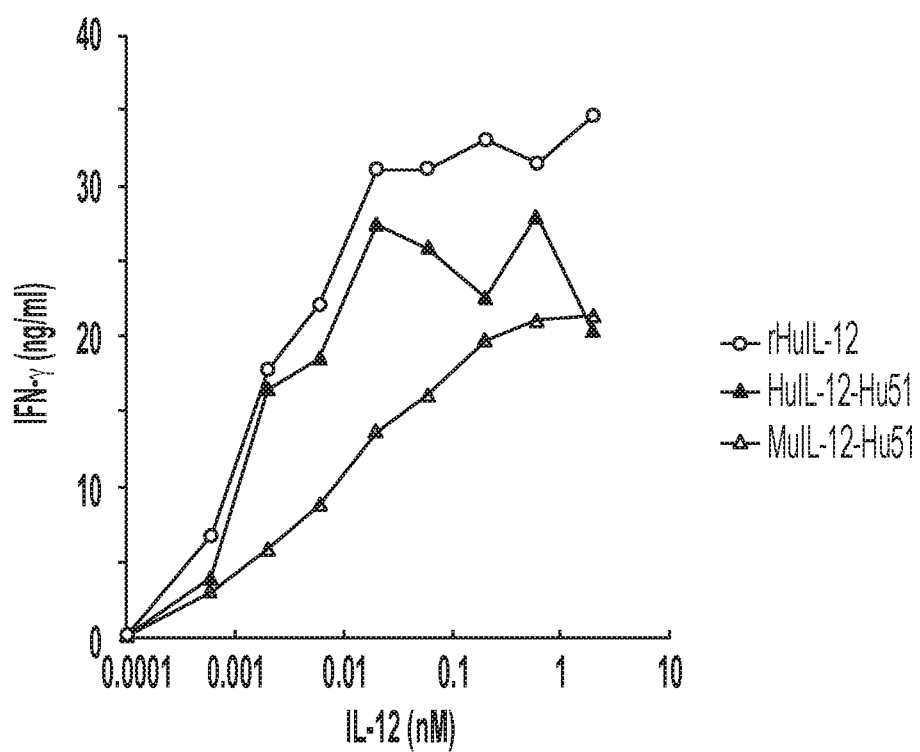
FIG. 2 is an exemplary graph showing the biological activity of IL-12 and selected chimeric proteins comprising an IL-12 portion with respect to IL-12 mediated IFN-γ secretion.

In a further set of experiments, haNK cells (i.e., aNK cell derivatives expressing high-affinity CD16 and intracellularly retained IL-2) were cultured overnight in the presence of human recombinant IL-12 (rHuIL-12), and selected human or murine recombinant IL-12-Ab chimeric constructs (HuIL-12/Hu51-4 and MuIL-12/Hu51-4) having the sequence of SEQ ID NO:1 and SEQ ID NO:2 or SEQ ID NO:1 and SEQ ID NO:3. Cells were cultured by seeding $2.5 \times 10^5$ cells into a 24 well plate, X-Vivo 10 containing 5% human serum. The cell culture supernatants were then collected and human IFN-γ measured by ELISA. Remarkably, constitutive IL-2 exposure via intracellular expression of IL-2 rendered haNK cells sensitive to IL-12 signaling as can be readily taken from the graphs in FIG. 2. Indeed, exposure to IL-12 in various forms resulted in significant IFNγ secretion for both murine and human IL-12. As expected, human IL-12 produced somewhat stronger IFNγ secretion in the haNK cells than murine IL-12.

Figure 3:
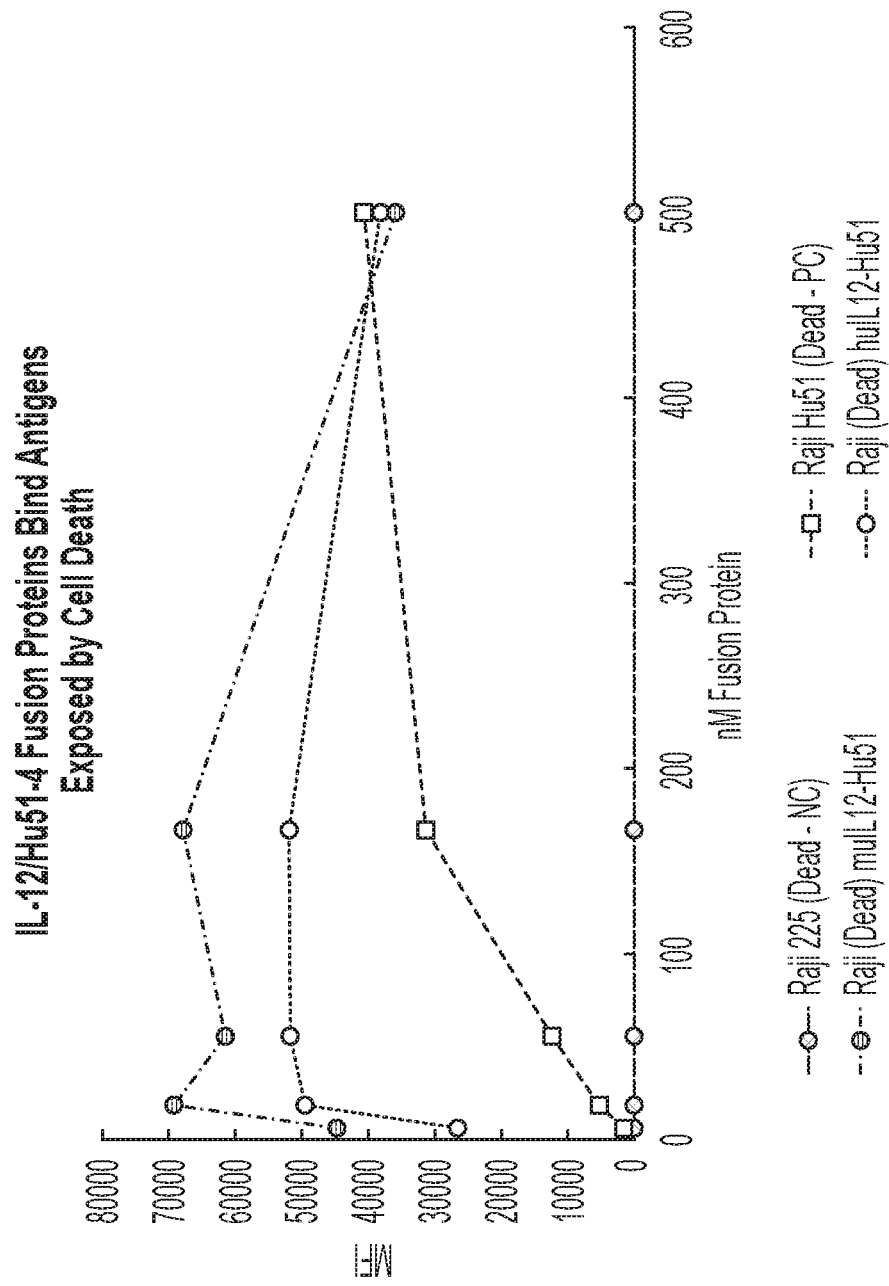
FIG. 3 is an exemplary graph showing binding of selected chimeric proteins comprising an IL-12 portion linked to antigens exposed by cell death.

Binding specificity of chimeric proteins HuIL-12/Hu51-4 and MuIL-12/Hu51-4 towards necrotic cells was evaluated using dead Raji cancer cells (human Burkitt's lymphoma cells) and exemplary results are depicted in FIG. 3. Results are shown for negative control (NC), positive control (PC), and binding of HuIL-12/Hu51-4 and MuIL-12/Hu51-4 as indicated. As can be readily seen from the graph, both HuIL-12/Hu51-4 and MuIL-12/Hu51-4 avidly bound to the target antigens in the dead cells. Exemplary sequences for HuIL-12/Hu51-4 and MuIL-12/Hu51-4 are also depicted in FIG. 4.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Moreover, as used herein, the phrase "at least one of A and B" is intended to refer to 'A' and/or 'B', regardless of the nature of 'A' and 'B'. For example, in some embodiments, 'A' may be single distinct species, while in other embodiments 'A' may represent a single species within a genus that is denoted 'A'. Likewise, in some embodiments, 'B' may be single distinct species, while in other embodiments 'B' may represent a single species within a genus that is denoted 'B'.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus

What is claimed is:

1. A chimeric protein that comprises an IL-12 portion and a cancer cell targeting portion, wherein the chimeric protein comprises in a single polypeptide sequence a scIL-12 in which an IL-12α subunit and a IL-12β subunit are coupled to each other via a peptide linker, and in which the scIL-12 is coupled to an N-terminus of the cancer cell targeting portion, and wherein the cancer cell targeting portion comprises an antibody heavy chain having the sequence of amino acids 539-991 of SEQ ID NO: 2, and an antibody light chain having the sequence of amino acids 24-236 of SEQ ID NO: 3.

2. The chimeric protein of claim 1 wherein the IL-12 portion is covalently coupled to the cancer cell targeting portion via a peptide linker.

3. The chimeric protein of claim 1 wherein the peptide linker is a flexible (G4S)3 linker.

4. The chimeric protein of claim 1 bound to CD16 of an NK cell.

5. The chimeric protein of claim 1, wherein the chimeric protein comprises an IL-12 portion and a cancer cell targeting portion, wherein the chimeric protein comprises an amino acid sequence having at least 95% identity to SEQ ID NO: 2, and wherein the chimeric protein further comprises an antibody light chain having the sequence of amino acids 24-236 of SEQ ID NO: 3.

6. A pharmaceutical composition comprising the chimeric protein of claim 1.

7. The pharmaceutical composition of claim 6 further comprising an NK cell, wherein the NK cell is an IL-2 sensitized NK cell or a genetically modified NK cell that constitutively expresses IL-2.

8. The pharmaceutical composition of claim 7 wherein the NK cell is a genetically modified NK cell that constitutively expresses and intracellularly retains IL-2.

9. The pharmaceutical composition of claim 7 wherein the NK cell is a haNK cell, an aNK cell, or an NK92MI cell.

10. A composition comprising a chimeric protein and an NK cell wherein the chimeric protein comprises an IL-12 portion and a cancer cell targeting portion; and wherein the chimeric protein comprises in a single polypeptide sequence a scIL-12 in which an IL-12α subunit and a IL-12β subunit are coupled to each other via a peptide linker, and in which the scIL-12 is coupled to an N-terminus of the cancer cell targeting portion, and wherein the cancer cell targeting portion comprises an antibody heavy chain having the sequence of amino acids 539-991 of SEQ ID NO: 2, and an antibody light chain having the sequence of amino acids 24-236 of SEQ ID NO: 3.

11. The composition of claim 10 wherein the NK cell is a genetically modified NK cell that constitutively expresses and intracellularly retains IL-2.

12. The composition of claim 10 wherein the NK cell is a haNK cell, an aNK cell, or an NK92MI cell.

13. The composition of claim 10 wherein the chimeric protein is bound to the NK cell.

14. The chimeric protein of claim 10, wherein the chimeric protein comprises an IL-12 portion and a cancer cell targeting portion, wherein the chimeric protein comprises an amino acid sequence having at least 95% identity to SEQ ID NO: 2, and wherein the chimeric protein further comprises an antibody light chain having the sequence of amino acids 24-236 of SEQ ID NO: 3.

15. A method of targeting IL-12 to necrotic tumor cells, comprising administering the composition of claim 10 to a patient.

16. The method of claim 15 wherein the chimeric protein is administered at least 12 hours prior to administration of the NK cell, or wherein the chimeric protein is administered at least 12 hours after administration of the NK cell.

17. The method of claim 15 wherein the chimeric protein is contemporaneously administered with the NK cell.

* * * * *